United States Patent
Koch et al.

(10) Patent No.: US 10,913,729 B2
(45) Date of Patent: Feb. 9, 2021

(54) MIXTURES OF CANNABINOID COMPOUNDS, AND PRODUCTION AND USE THEREOF

(71) Applicant: SYMRISE AG, Holzminden (DE)

(72) Inventors: Oskar Koch, Göttingen (DE); Marcus Rudolf Götz, Oberweser (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/181,503

(22) Filed: Nov. 6, 2018

(65) Prior Publication Data

US 2019/0077783 A1  Mar. 14, 2019

Related U.S. Application Data

(62) Division of application No. 15/553,638, filed as application No. PCT/EP2016/054124 on Feb. 26, 2016.

(30) Foreign Application Priority Data

Feb. 26, 2015  (EP) .................................... 15156750

(51) Int. Cl.
| | |
|---|---|
| C07D 311/80 | (2006.01) |
| A61K 31/235 | (2006.01) |
| C07C 69/94 | (2006.01) |
| A61K 31/352 | (2006.01) |
| C07C 67/03 | (2006.01) |
| C07C 67/343 | (2006.01) |
| C07C 37/50 | (2006.01) |
| C07C 39/23 | (2006.01) |

(52) U.S. Cl.
CPC .......... *C07D 311/80* (2013.01); *A61K 31/235* (2013.01); *A61K 31/352* (2013.01); *C07C 37/50* (2013.01); *C07C 39/23* (2013.01); *C07C 67/03* (2013.01); *C07C 67/343* (2013.01); *C07C 69/94* (2013.01); *A61K 2300/00* (2013.01); *C07C 2601/14* (2017.05); *C07C 2601/16* (2017.05)

(58) Field of Classification Search
USPC ........................................................ 560/64
See application file for complete search history.

(56) References Cited

U.S. PATENT DOCUMENTS

| | | |
|---|---|---|
| 2010/0298579 A1 | 11/2010 | Herkenroth et al. |
| 2014/0271940 A1 | 9/2014 | Wurzer |

FOREIGN PATENT DOCUMENTS

| | | |
|---|---|---|
| DE | 102009019322 A1 | 11/2010 |
| EP | 1559423 A1 | 8/2005 |
| WO | 2009099868 A1 | 8/2009 |

OTHER PUBLICATIONS

Chinese Office Action dated Jan. 21, 2020 for corresponding Chinese Application No. 201680012612.X.
Indian Office Action dated Sep. 13, 2019 for corresponding Indian Application No. 201737030087.
Maureen Rouhi, "The Right Stuff", Science & Technology; vol. 81; No. 8; 2003; pp. 32-35.
International Search Report dated Apr. 28, 2016, for corresponding PCT Application No. PCT/EP2016/054124.
Cannabinoid: "Pharmaceutical Society of Japan NII-Electronic Library Service Cannabis. X.i) The Isolqtion and Structures of Four New Propyl", VgJ.Gill,f.Chem.Soc, Jan. 1, 1977 (Jan. 1, 1977), p. 1894, XP055204780, Retrieved from the Internet: URL: http://ci.nii.ac.jp/els/110003622725.p.
Bela Szabo: "Pharmacology of Cannabinoid Receptors", Internet Citation, Jan. 1, 2008 (Jan. 1, 2008), pp. 1-13, XP002638928, Retrieved from the Internet: URL: http://www.slideshare.net/qnbs7/pharma cology-of-cannabinoid-receptors.
Edery H et al: "Structure-Activity Relations in the Tetrahydrocannabinol Series. Modifications on the Aromatic Ring and in the Side-Chain", Arzneimittel Forschung. Drug Research, ECV Editio Cantor Verlag, Aulendorf, DE, vol. 22, No. 11, Jan. 1, 1972 (Jan. 1, 1972), pp. 1995-2003. XP008048340.
Spyros P. Nikas et al: "Regiospecifically deuterated (???)-??9-tetrahydrocannabivarins", Perkin Transactions 1, No. 22, Oct. 24, 2002 (Oct. 24, 2002), pp. 2544-2548, XP055225335.
Office Action dated Sep. 3, 2019 for corresponding parent U.S. Appl. No. 15/553,638.

(Continued)

*Primary Examiner* — Ana Z Muresan
(74) *Attorney, Agent, or Firm* — Polsinelli PC

(57) ABSTRACT

Described are specific mixtures comprising one or more (cannabinoid) compounds of the formula (A) and/or one or more of their salts as well was methods for their production.

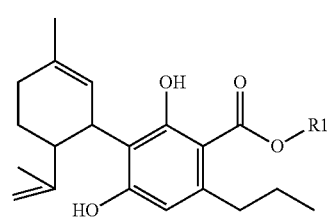

(A)

Further described are a compound of the formula (A), a salt of the formula (A) and a corresponding mixture for use as a medicament or, respectively, for use in a method for therapeutic treatment of the human or animal body.

Described are also corresponding pharmaceutical formulations, cosmetic preparations and preparations for pleasure and/or nutrition, suitable for consumption, as well as methods for producing CBDV and THCV.

15 Claims, 6 Drawing Sheets

(56) References Cited

OTHER PUBLICATIONS

Yukihiro Shoyama, "Cannabis X [1)] The Isolation and Structures of Four New Propyl Cannabinoid Acids, Tetrahydrocannabivarinic Acid and Cannabigerovarinic Acid, from Thai Cannabis, 'Meao Variant'", Chem. Pharm. Bull., vol. 25, No. 9, 1977, pp. 2306-2311.

MIXTURES OF CANNABINOID COMPOUNDS, AND PRODUCTION AND USE THEREOF

CROSS-REFERENCE TO RELATED APPLICATIONS

This application is a Divisional of U.S. application Ser. No. 15/553,638 filed on Aug. 25, 2017, which is the National Phase filing under 35 U.S.C. § 371 of PCT/EP2016/054124 filed on Feb. 26, 2016. This application also claims priority to European Application No. 15156750.0 filed in Europe on Feb. 26, 2015. The entire contents of each of these applications are hereby incorporated by reference.

The present invention relates to specific mixtures comprising one or more (cannabinoid) compounds of the formula (A) and/or one or more of their salts

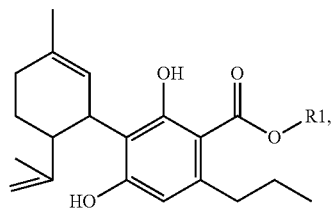

(A)

preferably one or more (cannabinoid) compounds of the formula

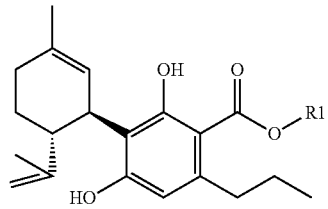

and/or one or more of their salts (of this preferred compound), as well as methods for their production. For the meaning of substituent R1, see below.

For the subsequent text applies: Embodiments, that relate to a compound of formula (A) (and/or their salts) or, respectively, comprise such a compound (and/or their salts) also relate, each in a preferred embodiment, to embodiments relating to or, respectively, comprising a compound of the previously described as preferred (cannabinoid) compounds (and/or their salts). The meaning of substituent R1 in the preferred compound results from the meaning of the substituent R1 for the compounds of the formula (A).

The invention further relates to a compound of the above formula (A), a salt of the formula (A) and a mixture comprising one or more (cannabinoid) compounds of the formula (A) and/or one or more of their salts, each for use as a medicament or, respectively, for use in a method for therapeutic treatment of the human or animal body.

Furthermore, the present invention relates to a compound of formula (A) or, respectively, a salt of formula (A) or, respectively, a mixture comprising one or more cannabinoid compounds of formula (A) and/or one or more of their salts for specific use in a method for therapeutic treatment of the human or animal body for achieving an effect selected from the group consisting of appetizing effect, antiemetic effect for the inhibition of nausea and vomiting, reduction of muscular cramps and spasticities, alleviation of pain symptoms, alleviation of migraine symptoms, reduction of the intraocular pressure in the case of a glaucoma, improved sentiment, immune stimulation and/or antiepileptic effect.

The present invention further relates to a pharmaceutical formulation comprising one or more compounds of the formula (A) or comprising one or more of their salts or comprising a mixture comprising one or more (cannabinoid) compounds of the formula (A) and/or one or more of their salts, preferably selected from the group consisting of solid galenic forms, lozenges, capsules, granulates, powders, suppositories, boiled sweet, chewing gums, semisolid forms, inhalants, injectables, implants and patches containing active ingredients.

Furthermore, the present invention relates to cosmetic preparations and preparations for nutrition and/or pleasure, suitable for consumption and comprising one or more compounds of the formula (A) and/or salts thereof (as described herein).

The present invention also relates to new methods for producing selected cannabinoids.

Further, the present invention relates to certain compounds of the formula (A) and their salts (as described below and in particular in the patent claims), which are new over the state of the art.

Further aspects of the present invention emerge from the subsequent specification as well as the attached patent claims.

Since the discovery of the endogenous cannabinoid system and its functional relevance for regulating and modulating the immune as well as nervous system, a constant need for natural and synthetic canabinoids exists for its selective pharmaceutical control. In particular and due to their different medical functions, the need exists for targeted separate stimulation of the cannabinoid receptors CB1, which are found predominantly in neurons, with the highest density in the basal ganglia, in the hippocampus and in the cerebellum, and the canabinoid receptors CB2, which are found predominantly on cells of the immune system and on cells involved in bone formation and loss.

The cannabinoid receptors CB1 and CB2 are considered as accepted target site for molecules with canabinoid structure. Although even further receptors are thought of as potential CB3 receptor, it is assumed that the main effects are imparted by CB1 and CB2. Delta-9-THC, endogenous cannabinoids and a variety of synthetic cannabinoids link to said receptors and carry out effects on the cells via those receptors (Pertwee, R. G. et al. Pharmacol. Rev. 2010, 62, 588-631).

CB1 and CB2 are members of the superfamily of the G-protein coupled receptors (GPCRs). More precisely the receptors inhibit the adenylate cyclase via the heteromere G-protein and activate the mitogen activated protein kinase (Howlett, A. C. et al. Pharmacol. Rev. 2002, 54, 161-202; Howlett, A. C. Handb. Exp. Pharmacol. 2005, 168, 53-79). It is further described for the CB1 receptor that it can modulate potassium currents via A-type ion channels and calcium currents via N- as well as P/Q-type channels. Furthermore, CB1 receptors can transfer signals via $G_s$-Proteins to the expressing cells (Glass, M., Felder, C. C. J. Neurosci. 1997; 17, 5327-5333; Maneuf, Y. P., Brotchie, J. M. J. Pharmacol. 1997; 120, 1397-1398; Calandra, B. et al. Eur. J. Pharmacol. 1999; 374, 445-455; Jarrahian, A. et al. J. Pharmacol. Exp. Ther. 2004, 308, 880-886).

The ability of CB1 and CB2 to impart signals via $G_{i/o}$ and further downstream via the inhibition of the adenylate cyclase, is made use of in the so-called [$^{35}$S]GTP gammaS binding assay and the cAMP assay (Howlett, A. C. et al. *Pharmacol. Rev.* 2002, 54, 161-202; Pertwee, R. G. *Handb. Exp. Pharmacol.* 2005a, 168, 1-51) to examine binding and signal transfer of cannabinoids.

CB1 receptors possess an orthosteric as well as one or more allosteric binding sites, that may be potential target sites for ligands (Price, M. R. et al. *Mol. Pharmacol.* 2005a, 68, 1484-1495; Adam, L. et al. *17th Annual Symposium of the Cannabinoids*, 2007, S. 86; Horswill, J. G. et al. *J. Pharmacol.* 2007, 152, 805-814; Navarro, H. A. et al. *J. Pharmacol.* 2009, 156, 1178-1184). CB1 receptors are mainly found at the terminal ends of central and peripheral neurons where they usually impart an inhibition of excitatory and inhibitory neurotransmitters (Howlett, A. C. et al. *Pharmacol. Rev.* 2002, 54, 161-202; Pertwee, R. G., Ross, R. A. *Prostaglandins Leukot Essent Fatty Acids*, 2002, 66, 101-121; Szabo, B., Schlicker, E. *Handb. Exp. Pharmacol.* 2005, 168, 327-365). The distribution of those receptors within the central nervous system is in such a way that their activation can influence different cognitive processes (e.g. attentiveness and memory, diverse motor functions and pain recognition).

CB2 receptors are, as already mentioned, predominantly localized in immune cells. Upon activation, they modulate cell migration and release of cytokines within and outside the brain (Howlett, A. C. et al. *Pharmacol. Rev.* 2002, 54, 161-202; Cabral, G. A., Staab, A. *Handb. Exp. Pharmacol* 2005, 168, 385-423; Pertwee, R. G. *Handb. Exp. Pharmacol.* 2005a, 168, 1-51).

Furthermore, there is evidence that first, CB1 receptors are expressed by non-neuronal cells (including immune cells) (Howlett, A. C. et al. *Pharmacol. Rev.* 2002, 54, 161-202) and second, that CB2 receptors are expressed by several cells within and outside the brain (Skaper, S. D. et al. *Proc. Natl. Acad. Sci. USA* 1996, 93, 3984-3989; Ross, R. A. et al. *Neuropharmacology* 2001a, 40, 221-232; Van Sickle, M. D. et al. *Science* 2005, 310, 329-332; Wotherspoon, G. et al. *Neuroscience* 2005, 135, 235-245; Beltramo, M. et al. *Eur. J. Neurosci.* 2006, 23, 1530-1538; Gong, J. P. et al. *Brain Res.* 2006, 1071, 10-23; Baek, J. H. et al. *Acta Otolaryngol* 2008, 128, 961-967).

Known compounds, that demonstrably show an affinity to the above-mentioned receptors CB1 and CB2, are cannabidiol (CBD) originating inter alia from representatives of the female *cannabis Cannabis sativa* and *Cannabis indica* as well as certain chemical derivates thereof.

*Cannabis* belongs to the Cannabidaceae family. The botanic and chemotaxonomic classification of the genus *Cannabis* is made by means of two different approaches. Schultes et al. distinguishes three kinds *Cannabis sativa* Linnaeus, *Cannabis indica* LAM. and *Cannabis ruderalis* (Schultes, R. E. et al. *Harvard University Botanical Museum Leaflets* 1974, 23, 337-367). Others only name the one kind *Cannabis sativa* L. from sub-kind *Cannabis sativa* ssp. *sativa* and ssp. *Indica*.

According to a technical-legal perspective, a drug type and a fiber type is differentiated, wherein the differentiation is based on the proportions of the main cannabinoids CBD and Delta-9-THC.

Different cannabinoid compounds and methods for their production are known in prior art.

Korte et al. (Tetrahedron Letters 1969, 3, 145-7) describe cannabidivarin as a first and suggest a synthesis analogous to the one of Petrzilka et al. (Helvetica Chimica Acta 1967, 50, 719-723). Hereby, however, only small yields can be achieved.

Additionally, Crombie et al. (Phytochemistry 1975, 4, 11975) describe the synthesis of cannabidivarin in a miniature scale, as a condensation of divarin with para-mentadienole. The synthesis in dried $CH_2Cl_2$, saturated with PTSA, is however little selective and the expected products arise in an uneconomic relation. Tetrahydrocannabidivarin (described as Delta-1-Tetrahydrocannabivarol here) arises in the same way applying higher temperature in uneconomic concentration in a mixture of materials.

Based upon this, various methods to produce cannabinoids have been developed.

WO 2006/136273 describes a method to produce dronabinol (in the document described as: (6aR-trans)-6a,7,8,10a-tetrahydro-6,6,9-trimethyl-3-pentyl-6H-dibenzo[b,d]pyran-1-ol, $\Delta^9$-Tetrahydrocannabinol ($\Delta^9$-THC), according to IUPAC also called (6aR,10aR)-6,6,9-trimethyl-3-pentyl-6a,7,8,10a-tetrahydro-6H-benzo[c]chromen-1-ol today or called Delta-9-Tetrahydrocannabinol, Delta-9-THC oder $\Delta$-9-THC) by cyclization of cannabidiol (CBD) (2-[1R-3-methyl-6-(1-methylethenyl)-2-cyclohexen-1-yl]-5-pentyl-1, 3-benzoldiol) to Delta-9-THC. The described method is characterized by providing cannabidiol (CBD) in an organic solvent and by cyclising it in presence of a molecular sieve by heating to Delta-9-THC. In WO 2006/136273 it is determined that the used molecular sieve has, in addition to the already described drying properties, also strong catalytic properties which are paramount in the described reaction. Cyclizations, which are only accomplished in presence of a Lewis acid catalyst, are usually significantly slower and achieve lower yields of Delta-9-THC than cyclizations, which are accomplished in presence of a molecular sieve.

The literature describes further variants of syntheses as e.g. by Crombie et al. (*Chem. Research* 1977, 114, 1301-1345). Newer methods of synthesis are disclosed inter alia in EP 23 14 580. The method for producing cannabinoids described therein shall be applicable for all stereoisomers and homologues of cannabinoids and consist of two or, respectively, three chemical steps of synthesis. Thereby and in a first step, alkylresorcylacid esters (6-alkyl-2,4-dihydroxybenzoicacid esters) with unsaturated carbohydrates, alcohols, ketones (or, respectively, their derivates such as enole esters, enole ethers and ketals) are condensed into the respective and in position 3 substituted 6-alkyl-2,4-dihydroxybenzoicacid esters. Furthermore, EP 25 78 561 describes the reaction of menthadienol or ist derivates with 6-alkyl-2,4-dihydroxybenzoicacid esters. As preferred Lewis acid catalysts metal triflates are used. These include e.g. scandium- or, respectively, Zn-trifluorine-sulfonate. In the two publications, the intermediate products produced in the first step and with an ester function are subjected in a second step to a decarboxylating saponification, whereby the respective ester free cannabinoids arise. Where necessary, an acidic catalysed redistribution is carried out in a third step. This isomerisation can be the closure of the ring of the pyran ring of CBDV into THCV.

U.S. Pat. No. 5,342,971 describes a method to produce dronabinol and related dibenzo[b,d]pyrans. These are produced according to the abstract by heating of a dihydroxybenzoicacid derivate in presence of a Lewis acid catalyst and an inert unpolar solvent, in which the dihydroxybenzoicacid is soluble, but the Lewis acid catalyst is insoluble or marginally soluble. A typical embodiment includes the production of intermediates useful for the synthesis of dronabinol and related dibenzo[b,d]pyrans.

However, no further synthesis of cannabinoid compounds is known, which leads to a 5-propylbenzene structure or, respectively, a 3-propyl substituted benzochromen basic structure.

It was the primary task of the present invention to indicate cannabinoid active substances or mixture of substances (and methods for their production), preferably those showing an advantageous CB1- or, respectively, CB2 affinity, wherein particularly preferably one of the said two receptor affinities prevails the other. The method of production should preferably have a high yield of space and time in combination with ecological advantages (preferably the use of non chlorinated solvents). In particular a new method to produce CBDV, preferably from formerly unknown cannabinoid esters, as well as THCV should be found.

Figure 1:
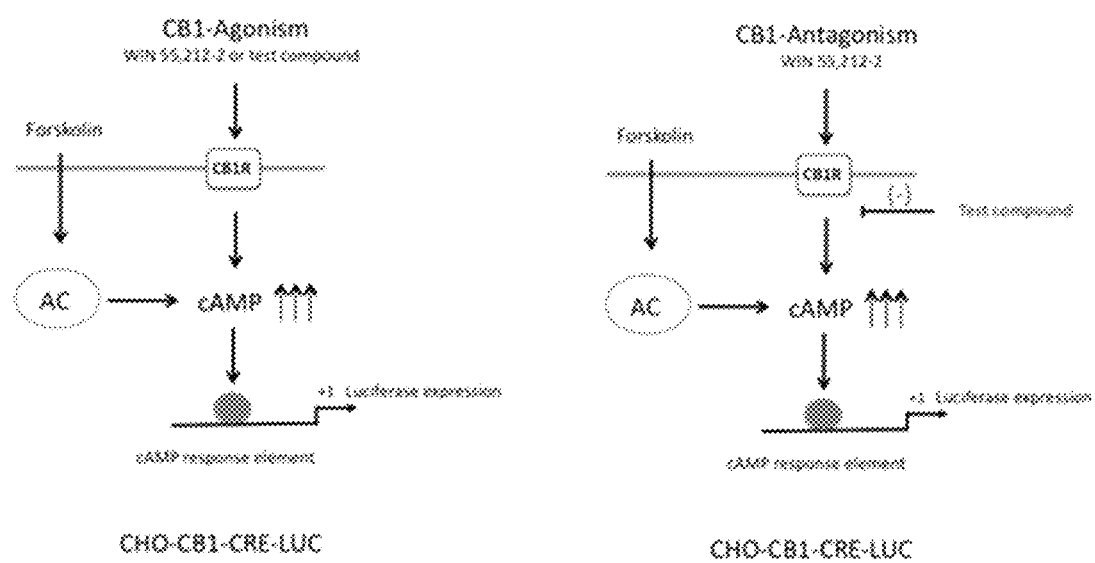
FIG. 1 provides an analysis scheme signal transmission at CB1 and CB2 transfected CHO cells.

The substances or mixture of substances for being indicated should thereby be possible to be applied preferably as pharmaceutical or in a method for therapeutic treatment of the human or animal body for achieving an effect selected from the group consisting of appetizing effect, antiemetic effect for the inhibition of nausea and vomiting, reduction of muscular cramps and spasticities, alleviation of pain symptoms, alleviation of migraine symptoms, reduction of the intraocular pressure in the case of a glaucoma, improved sentiment, immune stimulation and/or antiepileptic effect.

The present invention is inter alia based on the surprising realization that compounds of the formula (A) as well as their salts, wherein the substituent R1 in the formula (A) is an aliphatic rest with none or one, two, three or more than three hydroxyl groups, wherein the total number of C-atoms in the aliphatic rest R1 is not bigger than 15, preferably not bigger than 12, and
  wherein the aliphatic rest is
  saturated or unsaturated
  and
  branched or linear
  and
  acyclic or cyclic,
  providing that the compound(s) of the formula (A) or, respectively, the salt(s) thereof, in case R1 is an aliphatic rest with no hydroxyl group, is/are selected from the group consisting of the compounds cyclohexylcannabidivarinolat (CHCBDV) and hexylcannabidivarinolat (HCBDV) as well as their salts,
  show an advantageous binding affinity towards the cannabinoid receptors CB1 and CB2, whereby they are suitable for the application as a medicament or the application in a method for therapeutic treatment of the human or animal body.

The above and subsequently described advantageous or, respectively, surprising realizations or, respectively, properties apply for the preferred compound disclosed in paragraph 1 of the present text accordingly.

The invention thereby also relates to a compound of the formula (A) (as defined above and subsequently, in particular in the claims) or a salt of a compound of the formula (A) (as defined above and subsequently, in particular in the claims) or a mixture (as defined above and subsequently, in particular in the claims)
  (i) for the application as a medicament (pharmaceutical) or
  (ii) for the application in a method for therapeutic treatment of the human or animal body. The above said application as pharmaceutical or said application in a method for therapeutic treatment of the human or animal body (as well as subsequently said applications of such type or, respectively, specific applications as pharmaceutical or for application in a specific method for therapeutic treatment of the human or animal body) particularly preferably applies for the preferred compound disclosed in paragraph 1 of this text.

The application of one or more compounds of the formula (A) (as defined above and subsequently, in particular in the claims) or of one or more of their salts or of a corresponding mixture (as defined above and subsequently, in particular in the claims) as a medicament or, respectively, in a method for therapeutic treatment of the human or animal body particularly aims at the achievement of an effect selected from the group consisting of
  appetizing effect,
  antiemetic effect for the inhibition of nausea and vomiting,
  reduction of muscular cramps and spasticities,
  alleviation of pain symptoms,
  alleviation of migraine symptoms,
  reduction of the intraocular pressure in the case of a glaucoma,
  improved sentiment,
  immune stimulation
  and/or
  antiepileptic effect
  and/or
  as CB1 and/or CB2 receptor modulator.

The invention further relates to a pharmaceutical formulation, comprising one or more compounds of the formula (A) (as defined above and subsequently, in particular in the claims) or comprising one or more of their salts (as defined above and subsequently, in particular in the claims) or comprising a corresponding mixture (as defined above and subsequently, in particular in the claims). The pharmaceutical formulation according to the invention is thereby preferably selected from the group consisting of
  solid galenic forms,
  lozenges,
  capsules,
  granulates,
  powders,
  suppositories,
  boiled sweet,
  chewing gums,
  semisolid forms,
  inhalants,
  injectables,
  implants
  and
  patches containing active ingredients.

Alternatively, the pharmaceutical formulation exists in liquid form.

Preferred pharmaceutical formulations are:

Solid galenic forms (such as tablets (with coating and without, with modified release and without)), lozenges (with coating and without, with modified release and without), capsules (soft or hard gelatine capsules with modified release and without), granulates (with modified release and without), powders (with modified release and without, e.g. nose powder, ear powder), suppositories (with coating and without, with modified release and without), boiled sweet, chewing gums, semisolid forms (such as hydrophobic ointments including e.g. carbohydrate gels, lipogels, silicone gels, oleogels as well as water absorbing ointments including e.g. absorption bases, hydrophilic ointments, hydrophilic gels (hydrogels) or pastes, also nose ointments), inhalants (such as compressed gas metered-dose inhalers, powder inhalers, inhalers with sprayers, inhalation concentrates for inhaling), injectables and implants (e.g. on basis of liquid forms or of solid forms, which are suitable for the preparation of injection capable solutions or as such solutions themselves, or solid moulds, which enable a modified release), patches containing active ingredients, ear tampons.

Liquid forms are e.g. solutions, suspensions, emulsions, syrups (colloquially cough syrup), mouthwashes, gurgle solutions, throat sprays or nose sprays, nose drops, nasal rinsing solutions, ear drops, ear sprays and ear rinsing solutions.

Pharmaceutical formulations comprising one or more compounds of the formula (A) (as defined above and subsequently, in particular in the claims) and/or one or more of their salts (as defined above and subsequently, in particular in the claims) and/or corresponding mixtures (as defined above and subsequently, in particular in the claims) for application as pharmaceutical or for application in a method for therapeutic treatment of the human or animal body preferably contain one or more ingredients of the following groups: fillers (e.g. cellulose, calcium carbonate), plasticizers and trickling substances (e.g. talc, magnesium stearate), coatings (e.g. polyvinylacetatphtalate, hydroxypropylmethylcellulosephtalate), disintegrants (e.g. starch, cross-linked polyvinylpyrrolidone), softeners (e.g. triethylcitrate, dibutylphtalate), substances for granulation (lactose, gelatine), retardation (e.g. poly(meth)acrylicacidmethyl/ethyl/2-trimethyl-aminoethyl ester co-polymerisates in dispersion, vinylacetate/crotonic acid co-polymerisates), compaction (e.g. micro crystalline cellulose, lactose), solvents, suspension or dispersing agents (e.g. water, ethanol), emulsifiers (e.g. cetyl alcohol, lecithin), substances for changing rheological properties (silicondioxide, sodium alginate), substances for microbial stabilisation (e.g. benzalkonium chloride, potassium sorbate), preservatives and antioxidants (e.g. DL-alpha-tocopherol, ascorbic acid), substances for changing the pH value (lactic acid, citric acid), propellants and inert gases (e.g. fluorinated chlorinated hydrocarbons, carbon dioxide) dyes (iron oxides, titanium dioxide), ointment raw materials (e.g. paraffins, beeswax), and others as they appear in technical literature (e.g. Schmidt, P. C., Christin, I. "*Wirk-und Hilfsstoffe für Rezeptur, Defektur und Großherstellung*", 1999, Wissenschaftliche Verlagsgesellschaft mbH Stuttgart or Bauer, K. H., Frömming, K-H., Führer, C. "*Lehrbuch der Pharmazeutischen Technologie*", 8. *Auflage*, 2006, Wissenschaftliche Verlagsgesellschaft mbH Stuttgart).

The preferably used amounts of one or more compounds of the formula (A) (as defined above and subsequently, in particular in the claims) and/or of one or more of their salts (as defined above and subsequently, in particular in the claims) and/or of corresponding mixtures (as defined above and subsequently, in particular in the claims) as well as above mentioned ingredients in a pharmaceutical formulation can, depending on type and purpose of the particular formulation, easily be determined by the person skilled in the art by simple trying.

The above said on pharmaceutical formulations applies for the preferred compound disclosed in paragraph 1 accordingly.

The herein described compounds of the formula (A) and their salts are advantageously also suitable for application in cosmetic preparations. Further they are suitable to be applied in preparations for pleasure and/or nutrition, suitable for consumption. The preferably used amounts for such preparations of one or more compounds of the formula (A) (as defined above and subsequently, in particular in the claims) and/or of one or more of their salts (as defined above and subsequently, in particular in the claims) and/or of corresponding mixtures (as defined above and subsequently, in particular in the claims) can, depending on type and purpose of the particular formulation, easily be determined by the person skilled in the art by simple trying. The other ingredients of such preparations are ingredients typical for such preparations.

The comprised amounts of (a) compound(s) of the formula (A) and/or its/their salt(s) in a formulation or, respectively, preparation according to the invention is preferably sufficient to achieve one or more effects selected from the group consisting of appetizing effect, antiemetic effect for the inhibition of nausea and vomiting, reduction of muscular cramps and spasticities, alleviation of pain symptoms, alleviation of migraine symptoms, reduction of the intraocular pressure in the case of a glaucoma, improved sentiment, immune stimulation and antiepileptic effect and/or as CB1 and/or CB2 receptor modulator by the application or, respectively, with use or consumption.

The present invention also relates to a mixture comprising one or more compounds of the formula (a) and/or one ore more of their salts,

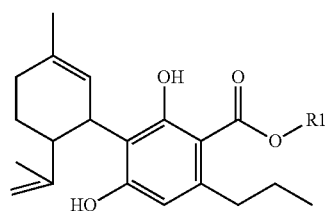

(A)

preferably one or more (cannabinoid) compounds of the formula

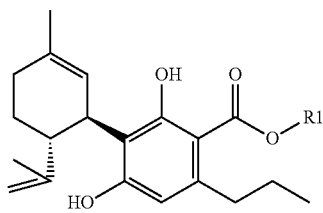

and/or one or more of their salts, wherein the substituent R1 is an aliphatic rest with none or one, two, three or more than three hydroxyl groups, wherein the total number of C-atoms in the aliphatic rest R1 is not bigger than 15, preferably not bigger than 12, and wherein the aliphatic rest is saturated or unsaturated and branched or linear and acyclic or cyclic, providing that the compound(s) of the formula (A) or, respectively, the salt(s) thereof, in case R1 is an aliphatic rest with no hydroxyl group, is/are selected from the group consisting of the compounds cyclohexylcannabidivarinolat (CHCBDV) and hexylcannabidivarinolat (HCBDV) as well as their salts, wherein in the mixture the molar ratio of the total amount of compounds of the formula (A) and their salts to the amount of compounds of the formula (V) (cannabidivarin, CBDV) (if present)

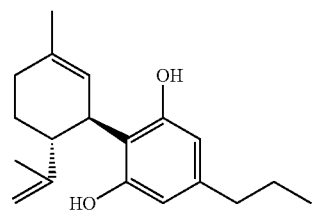

(V)

is bigger than 1:1, preferably bigger than 5:1, particularly preferably bigger than 10:1, and simultaneously the molar ratio of the total amount of compounds of the formula (A) and their salts to the amount of compounds of the formula (III) ((−)-trans-methylcannabidivarinolat) (if present)

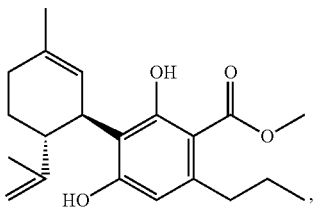

(III)

preferably to the amount of compound(s) of the formula (IX) (see below) (if present), is bigger than 1:1, preferably bigger than 5:1, particularly preferably bigger than 10:1.

Provided that the aliphatic rest R1 of a compound of the formula (A) contains one or more chiral centers, each of the possible configurations at the or, respectively, at each of the chiral center(s) is equal (R or S). If not stated otherwise in the particular case, an individual compound of the formula (A) with one or more chiral centers in the aliphatic rest and graphically presented in the present text equally describes all configuration isomers and all mixtures of configuration isomers of the presented compound, provided that these are presentable by adjustment of the configuration at the chiral center(s) of the aliphatic rest.

The present invention (in the above and subsequently mentioned embodiments preferably being defined as preferred embodiments) thus also relates to the following preferred specific compounds (and/or their salts) (for the meaning of the substituent R1 see the meaning of R1 in the compound of the formula (A)):

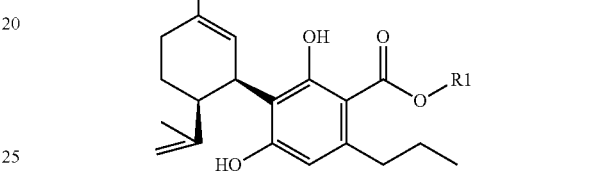

(i)

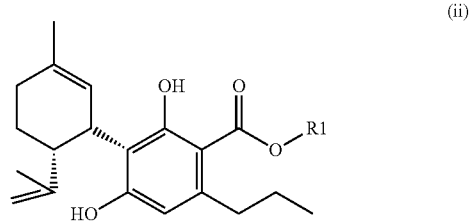

(ii)

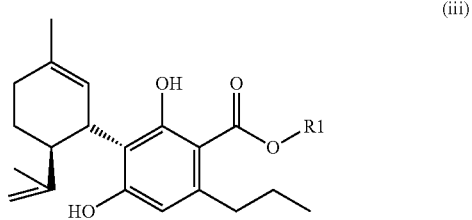

(iii)

and the particularly preferred compound (and/or their salts) of the formula

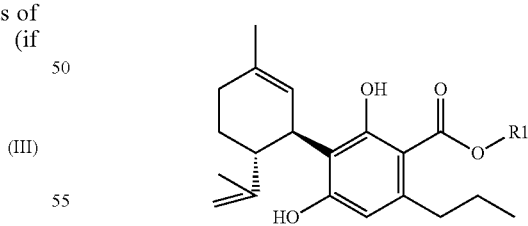

Depending on the desired embodiment and purpose, the mixtures according to the invention (as defined above and subsequently, in particular in the claims) can contain one or more of the ingredients as mentioned above in connection with pharmaceutical formulations according to the invention. Mixtures according to the invention can further be semi-finished products for the production of further compounds of the group of cannabinoids, which for their part again serve for the production of pharmaceutical formulations.

CBDV (compound of the formula (V)) can be obtained from a compound of the formula (A) by decarboxylating saponification according to EP 2 314 580 A1.

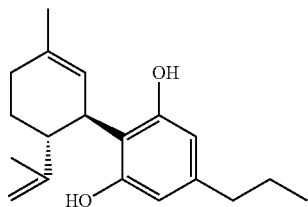

(V)

In a mixture according to the invention the total amount of compounds of the formula (A) and their salts prevails the possibly present CBDV.

The compound(s) of the formula (A) can be produced by transesterification of compounds of the formula (IX) (see below), for example by transesterification of the (–)-trans-methylcannabidivainolate of the formula (III).

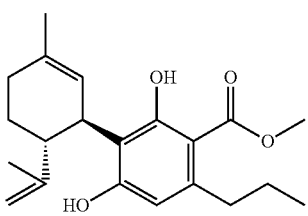

(III)

In a mixture according to the invention the total amount of compounds of the formula (A) and their salts prevails a possibly present compound of the formula (III), preferably the possibly present compounds of the formula (IX) (see below).

Therefore, in mixtures according to the invention CBDV and/or (–)-trans-methylcannabidivainolate can be present, their presence is however not compulsory.

If a mixture according to the invention comprises only a single compound of the formula (A) or, respectively, a salt of this single compound of the formula (A), it contains at least one further ingredient. For preferred ingredients see above.

Therefore, a mixture according to the invention comprises for example (i) a single compound or (ii) a single salt or (iii) various compounds or (iv) various salts or (v) a compound and a salt or (vi) various compounds and one or more salts or (vii) different salts of the same compound with the same pattern of deprotonization (however with different cations) or (viii) salts differing in their degree of deprotonization of the same compound with the same cations or (ix) salts differing in their degree of deprotonization of the same compound, however, with the same or different cations or (x) salts of different compounds with the same pattern of deprotonization and the same cations or (xi) salts of different compounds with different patterns of deprotonization and with the same or different cations or (xii) salts of different compounds with a different pattern of deprotonization and different cations.

A mixture according to the invention is preferably composed in a way that the proportion of the total amount of compounds of the formula (A) and their salts in the mixture accounts for 0.0001 to 100% by weight, preferably 0.001 to 100% by weight, particularly preferably 0.1 to 100% by weight, especially preferably 1 to 100% by weight with regard to the total weight of the mixture.

I.e. mixtures according to the invention, which do not only comprise a single compound of the formula (A) or, respectively, a single salt of this single compound of the formula (A), can be composed in a way that they exclusively (100% by weight) consist of compounds of the formula (A) and/or their salts.

To salts of compounds of the formula (A) according to the invention applies: if necessary, one or more hydroxyl groups of a compound of the formula (A) exist in deprotonated form. In addition to the (deprotonated) compound(s) of the formula (A) a corresponding amount of countercations exists, wherein these are preferably selected from the group consisting of: single positively charged cations of the first main-group and sub-group, ammonium ions, trialkylammonium ions, twice positively charged cations of the second main-group and sub-group as well as triple positively charged cations of the third main-group and sub-group, as well as mixtures thereof.

The phenolic hydroxyl groups of a compound of the formula (A) are regularly more acidic than hydroxyl groups in the aliphatic side chain (if present).

The corresponding amount of countercations (depending on their charge) is a result of the amount of deprotonated hydroxyl groups. For example for a compound of the formula (A) underlying such a salt with two phenolic hydroxyl groups arises that a twice negatively charged anion exists at complete deprotonization of these phenolic hydroxyl groups, whereof again results the amount of positive charges (here: two), which must be provided by the counterion(s). Particularly preferably these counterions are cations selected from the group consisting of $Na^+$, $K^+$, $NH_4^+$, $Ca^{2+}$, $Mg^{2+}$, $Al^{3+}$ and $Zn^{2+}$.

Described herein are also selected compounds of the formula (A), which are not yet known in prior art, namely the compounds cyclohexylcannabidivarinolat (CHCBDV), hexylcannabidivarinolat (HCBDV) and 2-hydroxyethylcannabidivarinolat (compound of the formula (IV)) (regarding these (new) compounds of the formula (A) see particularly the subsequently following example section, including synthesis examples as well as results of studies on the effect of these compounds of the formula (A) on cannabinoid receptors). The corresponding applies for their salts.

The above mentioned compounds and their salts belong to the compounds or, respectively, salts which are preferably used according to the present application.

A mixture according to the invention (as defined above and subsequently, in particular in the claims) is preferred—according to one aspect of the present invention—wherein the number of hydroxyl groups in the aliphatic rest R1 is one, two or three, preferably one or two. Due to the presence of the said one, two or three, preferably one or two, hydroxyl groups in the aliphatic rest, these compounds have the solubility required for the above or subsequently described applications or, respectively, reactions, however they do not have such a high amount of aliphatic hydroxyl groups that undesirable side reactions as e.g. elimination reactions in disturbing extent arise.

Particularly advantageous are mixtures according to the invention, wherein the aliphatic rest of the compound of the formula (A) is saturated and/or linear, preferably saturated and linear, as unsaturated aliphatic rests increase the risk of undesirable side reactions and branched aliphatic rests usually do not meet the steric requirements of mixtures according to the inventions in the same extent (especially for the application as pharmaceutical or the application in a method for therapeutic treatment of the human or animal body).

In a mixture according to the invention, it is preferred that the compound of the formula (A) is a compound of the formula (A-I)

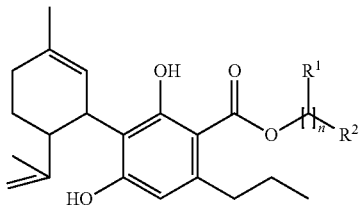
(A-I)

particularly preferably a compound of the formula

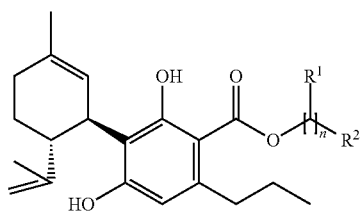

and/or one or more of their salts (of this particularly preferred compound), wherein applies:

each $R^1$ independently of the meaning of each of the others of the overall n rests $R^1$ is H, alkyl with one or two C-atoms or OH $R^2$ is H or OH n is an integral number in the range from 2 to 10, wherein at least one of the rests $R^1$ or the rest $R^2$ is OH.

Particularly preferred is a mixture according to the invention, wherein the compound of the formula (A) is a compound of the formula (A-II)

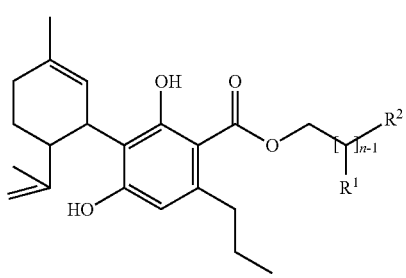
(A-II)

particularly preferred a compound of the formula

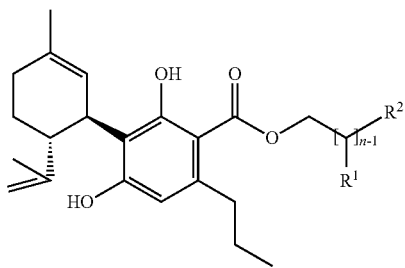

and/or one or more of their salts (of this particularly preferred compound)

wherein applies:

each $R^1$ independently of the meaning of each of the others of the overall n-1 rests $R^1$ is H, alkyl with one or two C-atoms or OH $R^2$ is H or OH n is an integral number in the range from 2 to 10, wherein at least one of the rests $R^1$ or the rest $R^2$ is OH.

It is generally preferred that there is a two bonded methylene group (—$CH_2$—) or (if $R^1$=H) a two bonded alkylene group in vicinity of the carboxyl group.

Especially preferred is a mixture according to the invention, wherein the compound of the formula (A) is (i) a compound of the formula
(A-III)

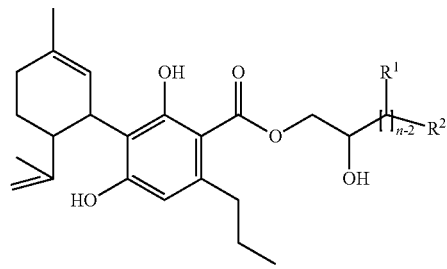
(A-III)

particularly preferably a compound of the formula

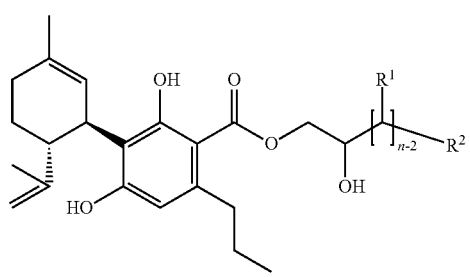

and/or one or more of their salts (of this particularly preferred compound), wherein applies:

each $R^1$ independently of the meaning of each of the others of the overall n-2 rests $R^1$ is H, alkyl with one or two C-atoms or OH $R^2$ is H or OH n is an integral number in the range from 2 to 10, preferably in the range from 3 to 10 wherein at least one of the rests $R^1$ or the rest $R^2$ is OH.

and/or (ii) a compound of the formula
(A-IV)

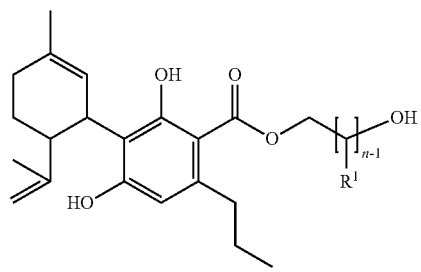

(A-IV)

particularly preferably a compound of the formula

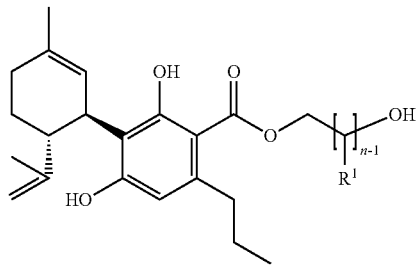

and/or one or more of their salts (of this particularly preferred compound), wherein applies:

each $R^1$ independently of the meaning of each of the others of the overall n-1 rests $R^1$ is H, alkyl with one or two C-atoms or OH n is an integral number in the range from 2 to 10.

Such compounds of the formulas (A-III) and (A-IV) have at least one hydroxyl group in the aliphatic side chain and a two bonded methylene group (—$CH_2$—) or, respectively, (if $R^1$ in formula (A-IV) is H) an alkylene group in vicinity to the carboxyl group.

A mixture according to the invention (as defined above and subsequently, in particular in the claims) is additionally preferred, wherein in the said formulas (A-I), (A-II), (A-III) or, respectively, (A-IV)

each $R^1$ independently of the meaning of each of the others of the rests $R^1$ is H or OH.

What is said above (and subsequently) regarding compounds of the formulas (A-I), (A-II), (A-III) or, respectively, (A-IV) applies for particularly preferred compounds of the formulas (A-I), (A-II), (A-III) or, respectively, (A-IV) accordingly.

Further preferred is a mixture according to the invention, which comprises one or more salts of the compounds of the formulas (A-I), (A-II), (A-III) or, respectively, (A-IV) (as defined above and subsequently, in particular in the claims).

Particularly preferred is a mixture according to the invention (as defined above and subsequently, in particular in the claims), wherein one/the compound of the formula (A) is a compound of the formula (IV):

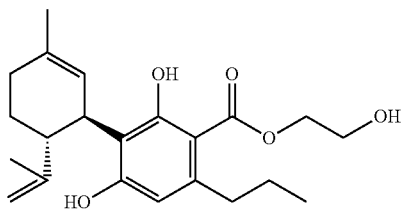

(IV)

The invention also relates to a method for producing a mixture according to the invention (as defined above and subsequently, in particular in the claims), with the following step:

Reacting a cannabidiolcarboxylicacid ester of the formula (IX)

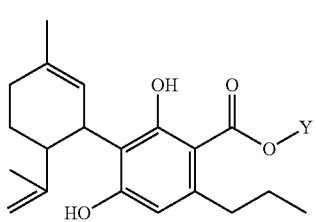

(IX)

particularly preferably a cannabidiolcarboxylicacid ester of the formula

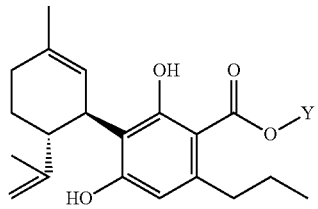

and/or one or more of their salts (of this particularly preferred cannabidiolcarboxylicacid ester), wherein Y is an organic rest, with an alcohol of the formula HO—X, wherein X is an aliphatic rest with none, or one, two, three or more than three hydroxyl groups, wherein the total amount of C-atoms in the aliphatic rest X is not bigger than 15, and wherein the aliphatic rest is
  saturated or unsaturated
and
  branched or linear
and
  acyclic or cyclic, providing that the alcohol of the formula HO—X, in case X is an aliphatic rest with no hydroxyl group, is selected from the group consisting of cyclohexanol and hexanol, wherein Y is different from X and selected in a way that an alcohol of the formula HO—Y formed during the reaction boils at 1013 hPa at a lower temperature than the used alcohol of the formula HO—X.

The product of the method according to the invention is a mixture according to the invention.

When reacting an ester of the formula (IX) with alkali in high-boiling solvents of the formula HO—X without presence of water, it was surprisingly noticed that this reaction does not directly lead to the corresponding carboxylic acid, but to the corresponding transesterification product, i.e. a compound of the formula (A). This compound could be isolated from the reaction mixture in high yield. In addition to their characteristics to function as modulators at CB1-/CB-2 receptors, these compounds of the formula (A) can further be used to produce CBDV and THCV.

Particularly preferred is a method according to the invention for producing a mixture according to the invention, wherein Y is an alkylgroup, which is preferably selected from the group consisting of methyl, ethyl, n-propyl, iso-propyl, n-butyl, sec-butyl, iso-buty, tert-butyl.

The alkylgroups methyl, ethyl, n-propyl, iso-propyl, n-butyl, sec-butyl, iso-buty, tert-butyl have turned out as advantageous rests Y in the reaction of the ester of the formula (IX) with an alcohol of the formula HO—X; their corresponding alcohols can be effectively removed from the reaction mixture with the subsequently described reaction conditions, which regularly leads to a particularly high yield as well as simplifies the requirements of the reaction construction.

Especially preferred is a method according to the invention for producing a mixture according to the invention, wherein the reaction of the ester of the formula (IX) with the alcohol of the formula HO—X occurs at a pressure which is lower than 1013 hPa, preferably at a pressure in the range from 5 to 500 hPa.

It is particularly advantageous to carry out the reaction in a vacuum instead of at normal pressure, since this enables an efficient removal of the arising alcohol of the formula HO—Y (e.g. methanol, ethanol, n-propanol, iso-propanol, n-butanol, sec-butanol, iso-butanol, tert-butanol) from the reaction mixture and thus supports the progress of the reaction. The alcohol of the formula HO—Y arising at transesterification is preferably removed from the reaction mixture by distillation.

Particularly preferred is a method according to the invention for producing a mixture according to the invention with the following step for producing the ester of the formula (IX) (the subsequently illustrated reaction scheme shows the reaction at the (preferred) example of the ester of the formula (III)):

Reacting menthadienol of the formula (I) with a divarin ester, particularly preferred with a divarinmethyl ester of the formula (II) to the corresponding ester of the formula (IX), particularly preferred to an ester of the formula (III),

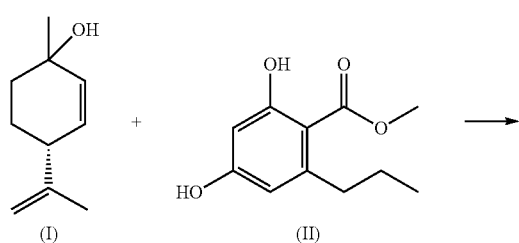

(I)   (II)

-continued

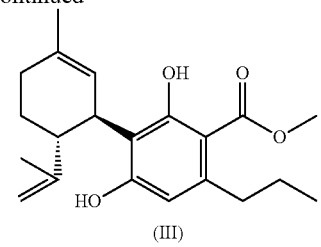

(III)

preferably in a continuous process.

It was surprisingly found that the reaction to the ester of the formula (IX) proceeds with a very high reaction speed, so that the method is feasible in a continuous way and with high yield of space and time. Within the corresponding study, a solution of the two starting products and a solution of a Lewis acid catalyst was continuously pumped in a stirred reaction chamber and subsequently directed into a saturated aqueous sodium bicarbonate solution, to hydrolyze the catalyst and to prevent a further reaction to side products.

The reaction can be performed in different solvents, as e.g. methylenchloride, chlorobenzene, toluene, xylene and cyclohexan, wherein methylenchloride and chlorobenzene showed considerable higher yields, due to industrial-hygienic reasons, however, high-boiling toluene is to be preferred.

Lewis acids as boron trifluoride*etherate, boron trifluoride*acetic acid, titanium tetrachloride, p-toluene sulphonic acid or methane sulfonic acid as well as metal triflates are suitable as catalysts, wherein boron trifluoride*etherate obtained particularly good results.

Particularly preferred embodiments result from the subsequently following example section (to this, see in particular the described steps 1 "coupling stepp" and 2 "transesterification"). As also resulting from the example section, the herein described compounds of the formula (A) can alternatively be obtained whilst the coupling step takes place after the transesterification. The present invention thus also relates to a method for producing a mixture according to the invention or, respectively, a compound of the formula (A) as described herein, in particular the new compounds cyclohexylcannabidivarinolat, hexylcannabidivarinolat and 2-hydroxyethylcannabidivarinolat with the following steps:

(a) Transesterification of a divarinacid ester, preferably of a divarinacidmethyl ester, with an alcohol of the formula HO—X
wherein
X is an aliphatic rest with none or one, two, three or more than three hydroxyl groups, wherein the total amount of C-atoms in the aliphatic rest X is not bigger than 15, and
wherein the aliphatic rest is
saturated or unsaturated
and
branched or linear
and
acyclic or cyclic,
providing that the alcohol of the formula HO—X, in case X is an aliphatic rest with no hydroxyl group, is selected from the group consisting of cyclohexanol and hexanol,
and
(b) Reaction of the divarinacid ester obtained by transesterification in step (a) with menthadienol to the corresponding compound of the formula (A), preferably to cyclohexylcannabidivarinolat, hexylcannabidivarinolat or 2-hydroxyethylcannabidivarinolat.

The invention further relates to a method for producing THCV or CBDV, comprising the production of a mixture according to the invention or, respectively, a herein described compound of the formula (A), wherein the mixture according to the invention is preferably produced with a method according to the invention (as described above).

It is particularly advantageous to synthesize THCV starting from a mixture according to the invention or, respectively, a herein described compound of the formula (A) (preferably by a method according to the invention (as defined above)), since the intermediately produced mixture or, respectively, compound according to the invention as well as the compound CBDV, which is usually subsequently produced intermediately, show individual biological activity themselves and can thus be removed from the process in a certain extent, to be used as cannabinoid active substances themselves. Furthermore, an interruption of the process, a storage of the intermediately produced mixtures according to the invention and a later continuation of the synthesis at the same or different place are advantageously possible.

Particularly preferred is a method according to the invention to produce THCV (or CBDV), wherein the produced mixture or, respectively, the compound of the formula (A) according to the invention is treated in a way that the compound of the formula (A) (present in the mixture) is decarboxylizingly saponified and the compound of the formula (V) (CBDV)

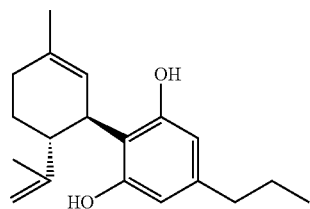

(V)

is produced,
preferably wherein the compound (V) being present after decarboxylizing saponification is cyclised to THCV.

Subsequently the present invention is further described by means of examples.

A. Studies on the Effect of Exemplary Compounds of the Formula (A) (as Described Herein) on Cannabinoid Receptors:

Binding Affinity:

In own studies, particularly the following compounds of the general formula (A) have been examined for their effect on cannabinoid receptors:

Cyclohexylcannabidivarinolat

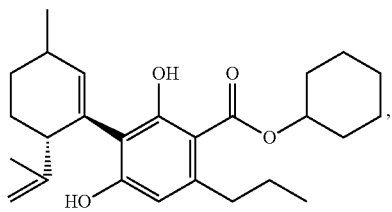

hexylcannabidivarinolat

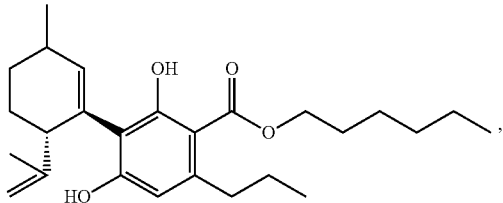

and
2-hydroxyethylcannabidivarinolat

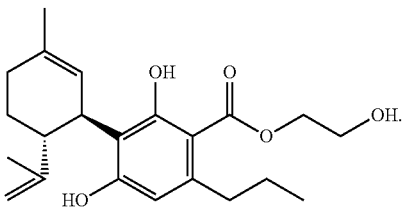

Compounds described above have been examined for their binding affinity and their resulting binding profile to CB1- and CB-2 receptors in competition studies. Such studies allow the comparison of the affinity of a substance (Ki-values) with the affinity of a classic ligand of cannabinoid receptors. The competition studies were performed in membranes of cells which have been transfected with CB1- or CB2-receptors.

Therefore, membranes of human cells were used, into which CB1- or CB2-receptors (RBHCB1M400UA and RBXCB2M400UA) were transfected with a Bmax and Kd value for CP55940 for CB1 or CB2 of for example 1.9 pmol/mg membrane protein and 0.18 nM for CB1 and 5.2 pmol/mg membrane protein and 0.18 nM for CB2.

In an exemplary experiment, the protein concentration of the CB1-receptor carrying membranes was 8.0 mg/ml and the protein concentration of the CB2-receptor carrying membranes was 4.0 mg/ml. These and further values resulted from the manufacturer's information on the membranes and are as easily comprehensible by the informed person skilled in the art as are the techniques with which the studies were performed. The membrane suspensions were diluted in a dilution of 1:20 with buffer solution (50 nM TrisCl, 5 nM $MgCl_2$, x$H_2O$, 2.5 nM EDTA, 0.5 mg/ml BSA and pH 7.4 for CB1 binding buffer; 50 nM TrisCl, 5 nM $MgCl_2$, x$H_2O$, 2.5 nM EGTA, 1 mg/ml BSA and pH 7.5 for CB2 binding buffer). [$^3$H]-CP55940 (144 Ci/mmol) was used as radioligand. Exemplary concentrations were hereby 0.10 nM with a volume of 200 µl for CB1 binding studies and 0.15 nM with a final volume of 600 µl for CB2 binding studies. The membranes were resuspended in the buffer and incubated with the radioligand and each substance for 90 min at 30° C. Unspecific binding was determined with the classic ligand WIN55212-2 and the 100% binding of the radioligand was determined by incubating the membrane without any other substance. After filtration of each approach, it was washed nine times with the respective binding buffer and dried subsequently. Radioactivity was determined with a suitable scintillation counter. Appropriate models are already known in literature (Granja, A. G. et al. *J. Neuroimmune Pharmacol.* 2012, 7, 1002-1016; Cumella, J. et al. *ChemMedChem.* 2012, 7, 452-463; Di Marzo, V. et al. 2000, *J. Neurochem.,* 2000, 74, 1627-1635).

The assessment of the components was performed in two steps. The first step consisted of a screening with a single high dose of each substance on its binding ability. The following table describes the percentage values for the binding to CB1 and CB2:

TABLE 1

Binding percentage of new cannabinoids to cannabinoid receptors

| Substance | $CB_1$ (% Binding) | $CB_2$ (% Binding) |
|---|---|---|
| cyclohexylcannabidivarinolat (CHCBDV) | 82.4% (n = 4) | 99.9% (n = 3) |
| hexylcannabidivarinolat (HCBDV) | 91.1% (n = 4) | 98.5% (n = 3) |
| 2-hydroxyethyl-cannabidivarinolat (HECBDV) | 43.3% (n = 5) | 95.0% (n = 3) |

Substances showing more than 40% binding and thus displacement of [$^3$H]-CP55940 (0.10 nM for CB1 and 0.15 nM for CB2) were examined for their competition for CB1 and CB2 in a second step, by incubating varying concentrations ($10^{-4}$-$10^{-11}$M) of the substances with [$^3$H]-CP55940 (0.10 nM for $CB_1$ and 0.15 nM for $CB_2$). The data resulting thereof were analyzed with a suitable statistics software (e.g. GraphPrism® Version 5.01). Table 2 shows the dissociation constants (Ki) for the substances as mean+/−standard error of the mean (SEM).

TABLE 2 dissociation constants of new cannabinoids

| Substance | Ki for $CB_1$ (nM) | Ki for $CB_2$ (nM) | Selectivity for $CB_2$ compared to $CB_1$ (fold) |
|---|---|---|---|
| cyclohexyl-cannabidivarinolat (CHCBDV) | 13.20 ± 0.85 | 4.62 ± 0.46 | 2.9 |
| hexylcannabidivarinolat (HCBDV) | 8.28 ± 0.69 | 9.91 ± 2.46 | 0.8 |
| 2-hydroxyethyl-cannabidivarinolat (HECBDV) | 5649.3 ± 3896.2 | 168.2 ± 39.4 | 33.6 |

The experiments were performed as triplicates.

Compared to that, the substance WIN55,212-2 which was used as classic non specific ligand as positive control for such an experiment shows a dissociation constant of 28.8±4.1 nM for CB1 and 3.7±0.2 nM for CB2 and thus corresponds to the listed values in the literature as e.g. Pertwee et al. 2010 (Pertwee, R. G. et al. *Pharmacol. Rev.* 2010, 62, 588-631): CB1: 1.89-123 nM and CB2: 0.28-16.2 nM.

The described compounds of the formula (A) bind to cannabinoid receptors in nM concentrations and thus in physiological doses. They are ligands for CB1 and preferably bind to CB2 receptors.

The dissociation constants are listed in the above tables. Hexylcannabidivarinolat (HCBDV) and Cyclohexylcannabidivarinolat (CHCBDV) show a strong binding to the receptors within the lower nanomolar range and are predestined as use in pharmacons. The selectivity of CHCBDV and 2-hydroxyethylcannabidivarinolat (HECBDV) for Cb2 receptors predestines these for the use as CB2 receptor modulators. Their different affinity can further be useful for being able to prevent substances with different potency and in different doses, which can be of use depending on the degree of severity of a disease.

Cannabinoids listed in literature and substances, which are not to be considered as the classic cannabinoids, are assigned to groups due to their affinity to CB1 or, respectively, CB2 receptors (Pertwee, R. G. et al. *Pharmacol. Rev.* 2010, 62, 588-631). The group membership and thus the pharmacodynamic mechanism determines the manner of the substances' effect.

While CBD having very low affinities (CB1 4,350->10,000 nM; CB2 2,399->10,000 nM) exerts a very weak effect, Δ-9-THC with CB1 5.05-80.3 nM and CB2 3.13-75.3 nM is a strong ligand for both receptors, which explains its strong effects (and side effects) on the central nervous system and simultaneously peripheral effects. The psychotropic effects of Δ-9-THC are attributed its complex interaction with the CB1 receptor. Activation of the CB1 receptor causes effects on the mind (and the circulation), whereas activation of the CB2 receptor does not seem to cause such effects, which is due to the CB2 receptor localization in the periphery (Atwood, B. K. *Prog. Neuropsychopharmacol. Biol. Psychiatry* 2012, 38, 16-20).

The herein described cannabinoids have a convenient and unique distribution of their binding affinity, see table 2. Their binding affinity to CB1 and CB2 receptors predestines the substances as pharmacons. The binding strength thereby seems to correlate to the polarity of the side chains at R1: Nonpolar rests seem to result in a stronger binding to CB1 and CB2 and tend to increase the selectivity for the CB2 receptor. Both, CHCBDV and HECBDV show a more selective binding to CB2. HCBDV shows a strong binding to CB1 and CB2 and can thus modulate both receptors in their activity.

Evidence for an advantageous effect of CB2 modulators in pathological situations which were hitherto not accessible to pharmacotherapy has grown strongly within the last years. The two most important indications for CB2 modulators are neuroinflammation and pain (Cheng, Y., Hitchcock, S. A. *Expert Opin. Invest. Drugs* 2007, 16, 951-965; Guindon, J., Hohmann, A. G. *J. Pharmacol.* 2008, 153, 319-334). Furthermore, herein described substances can also influence the following pathological situations by CB2 modulation: Systemic inflammation, osteoporosis, cancer, pathological conditions caused by transplantation, various pathological conditions of the central nervous system including drug addiction and anxiety states as well as liver diseases (Bab, I. et al. *Ann. Med.* 2009, 41, 560-567; Karsak, M. et al. *Science* 2007, 316, 1494-1497; Mallat, A., Lotersztajn, S. *Dig. Dis.* 2010, 28, 261-266; Nagarkatti, M. et al. *Trends Pharmacol. Sci.* 2010, 31, 345-350; Patel, K. D. et al. *Curr. Med. Chem.* 2010, 17, 1393-1410; Xi, Z. X. et al. *Nat. Neurosci.* 2011, 14, 1160-1166).

Signal Transmission at CB1 and CB2 Transfected CHO Cells:

Demuth et al. (2006) describe the transfer of signal by cannabinoid receptors. The manner of the transfer of signal has already been well described.

As the binding affinity of the above mentioned substances of the formula (A) (as described herein) is verified, their intrinsic activity was examined with a functional assay on cannabinoid receptor transfected cells. Therefore, CHO cells (immortalized "Chinese Hamster Ovary" cells) were transfected with CB1 and CB2 receptors by transfer of cDNA. The thereby obtained cells (CHO-CB1 and CHO-CB2) were transiently transfected with the Plasmid CRE-lux, which contains several (e.g. 6) consensus cAMP responsive elements (CRE) and firefly lucif erase (luc). The necessary techniques are accessible to the informed person skilled in the art by relevant literature.

To investigate the agonistic activity, the transfected cells (CHO-CB1-CREluc and CHO-CB2-CREluc) were treated and incubated either with increasing concentrations of the molecules according to the invention or with WIN55,212-2 (WIN), a classic non specific agonist at CB1 as positive control, and afterwards tested on their activity by addition of luciferin (a chemiluminescent substrate of the firefly luciferase). Forskolin, an activator of the adenylatcyclase, was used as positive control, as its activation of the cAMP pathway occurs independent of cannabinoid receptors. To investigate a possible antagonism at CB1 receptors, the CHO-CB1-CREluc cells were preincubated with the test substances and afterwards stimulated with WIN.

To examine the agonism at CB2 receptors, CHO-CB2-CREluc cells were treated for short time (e.g. 15 min) either with increasing concentrations of the molecules according to the invention or with WIN, also a classic non specific agonist at CB2 as positive control. Afterwards, forskolin was added and the mixture was incubated. To confirm the agonistic effect at CB2 receptors, furthermore, CHO-CB2-CREluc were incubated with the specific antagonist AM630 (Ross et al., 1999). After appropriate incubation time and subsequent lysis, the luciferase activity was measured. The background activity (buffer) was subtracted from the result in each case. FIG. 1 (Analysis scheme signal transmission at CB1 and CB2 transfected CHO cells) describes a possible analysis scheme for the presentation of the activity of substances according to the invention.

Substances according to the invention show an ability for binding to and modulation of cannabinoid receptors. Particularly preferably, they show a particularly convenient ratio of the activation (agonism) and inhibition (antagonism) of CB1 receptors and CB2 receptors.

These requirements are particularly met by HECBDV. In addition to its selective binding to the CB2 receptor, HECBDV shows an activation of the receptor and appears as selective agonist there, wherein CB1 receptors are simultaneously inhibited. CHCBDV and HCBDV strongly bind to CB1 and CB2 receptors. HCBDV shows a selective activation of CB1 receptors. CHCBDV appears as CB1 and CB2 agonist.

TABLE 3

Agonism and antagonism of new cannabinoids at cannabinoid receptors

| Substance | CB1 | CB2 |
|---|---|---|
| 2-hydroxyethyl-cannabidivarinolat (HECBDV) | − | ++ |
| hexylcannabidivarinolat (HCBDV) | ++ | 0 |
| cyclohexylcannabidivarinolat (CHCBDV) | ++ | ++ |

Figure 2:
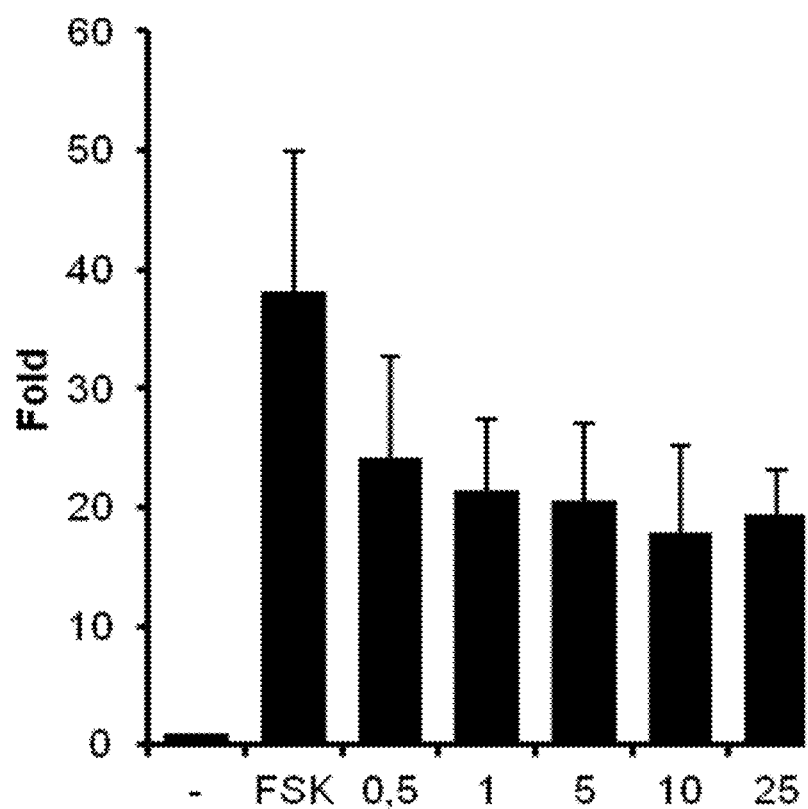
FIG. 2 illustrates the dose-dependent agonism of CHCBDV at the CB2 receptor.
Figure 3:
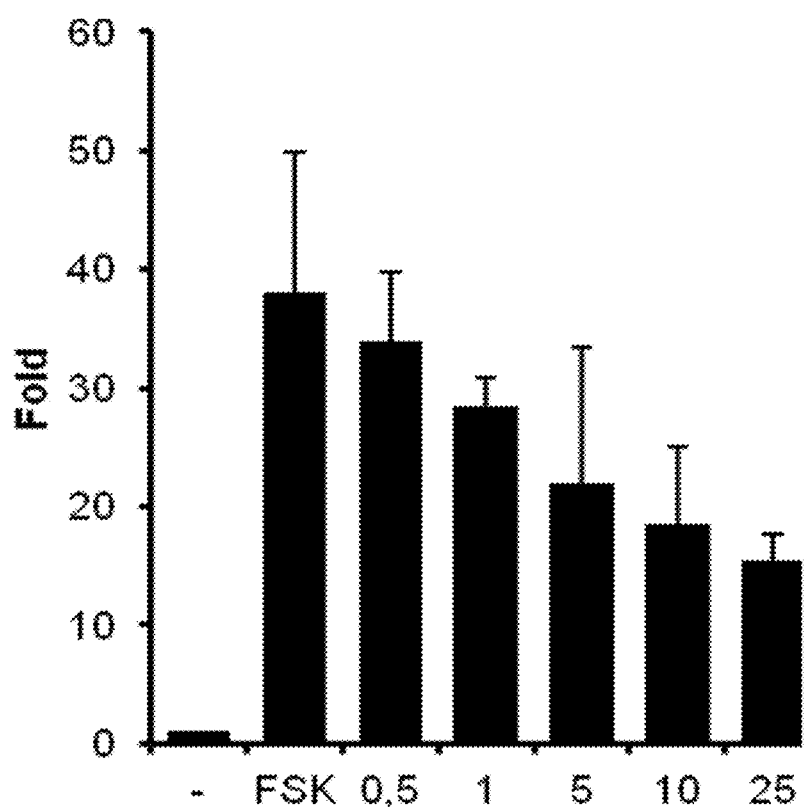
FIG. 3 illustrates the dose-dependent agonism of HECBDV at the CB2 receptor.
Figure 4:
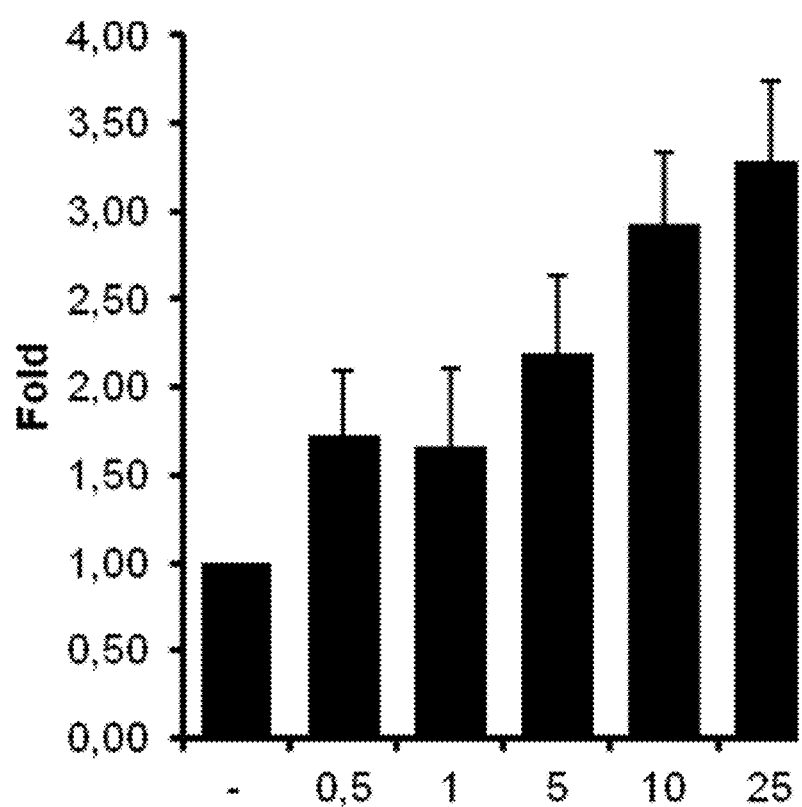
FIG. 4 illustrates the dose-dependent agonism of CHCBDV at the CB1 receptor.
Figure 5:
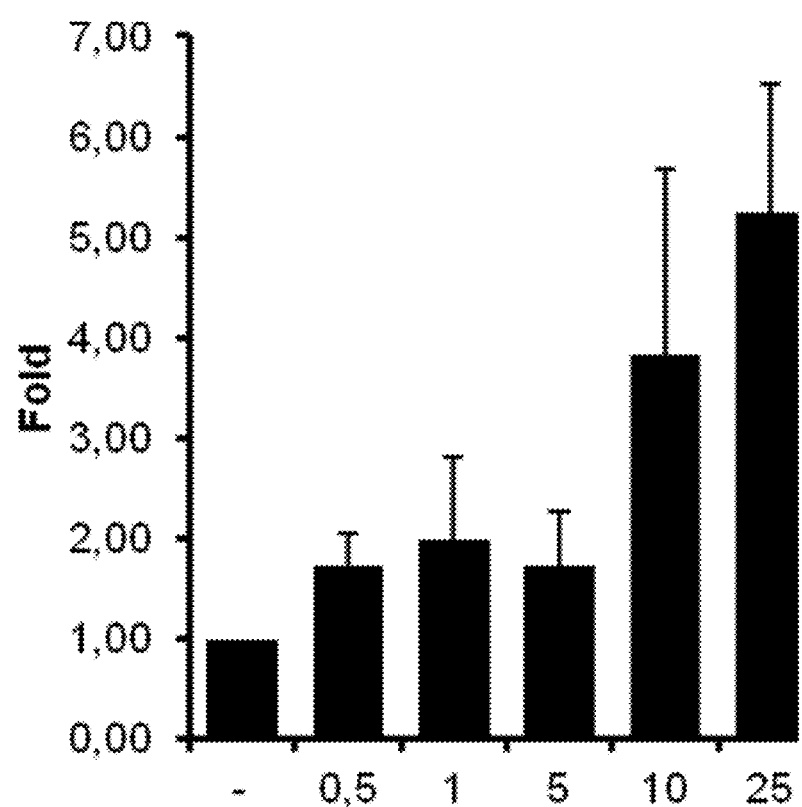
FIG. 5 illustrates the dose-dependent agonism of HCBDV at the CB1 receptor.
Figure 6:
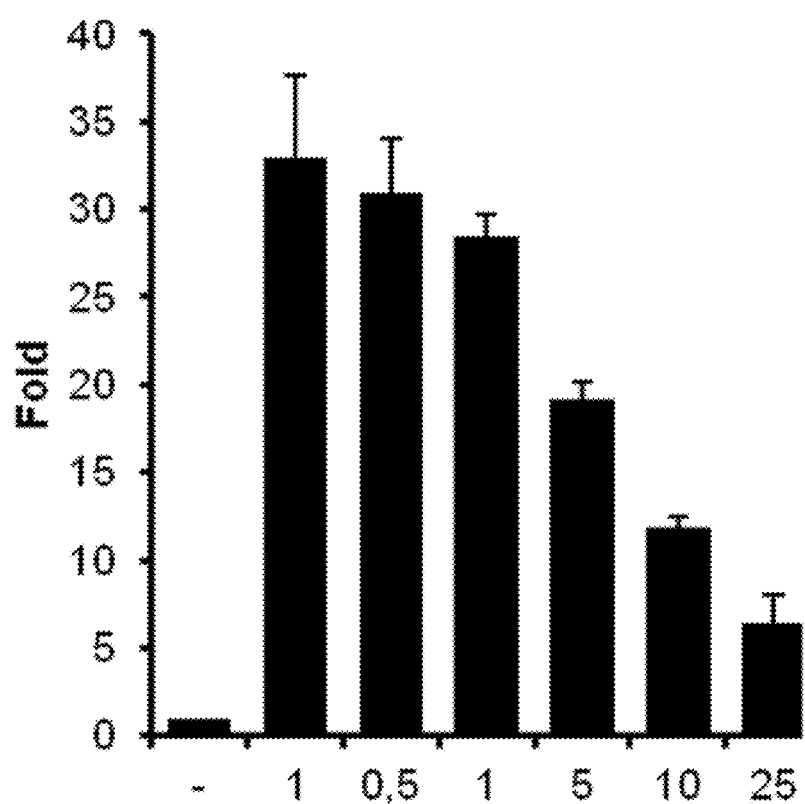
FIG. 6 illustrates the dose-dependent antagonism of HECBDV at the CB1 receptor.

Legend:
0: no effect
−: weak antagonism
−−: strong antagonism
+: weak agonism
++: strong agonism The agonism and/or the antagonism of the substances preferably arises in a dose-dependent manner, cf. FIGS. 2 to 6 (dosage in µM. Error bars represent standard deviation; FSK=Forskolin):

FIG. 2: Dose-dependent agonism of CHCBDV at the CB2 receptor.
FIG. 3: Dose-dependent agonism of HECBDV at the CB2 receptor.
FIG. 4: Dose-dependent agonism of CHCBDV at the CB1 receptor.
FIG. 5: Dose-dependent agonism of HCBDV at the CB1 receptor.
FIG. 6: Dose-dependent antagonism of HECBDV at the CB1 receptor.

Synthesis of CBDV and THCV Via
2-hydroxyethylcannabidivarinolat (IV) (Preferred Compound of the Formula (A) as Described Herein)

Step 1: Coupling Step (in the Continuous Method); Synthesis of Cannabidivarincarboxylicacid Methylester (III) (Preferred Ester of the Formula (IX) as Described Herein)

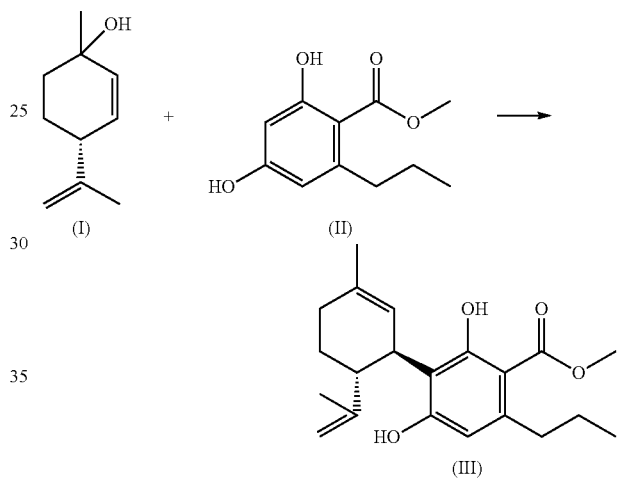

273 g (1.8 Mol) menthadienol and 377 g (1.8 Mol) divarinmethylester are dissolved in 1,450 g toluene (2,300 mL solution A) at room temperature (RT), likewise an adequate amount of borontrifluorid*etherate is dissolved in 540 g toluene at RT (710 mL solution B). Via two separated dosing pumps solution A with solution B are pumped in a stirred reaction cell with a constant stream in each case. From the reaction cell the reaction mixture flows via a PTFE-tube into a stirred 1,000 g sodium bicarbonate solution. The total reaction time is approx. 25 min. After the dosage, the hydrolysed reaction solution is stirred for approx. 1 h. The hydrolysed reaction solution is then transferred into a 5-Ltr. jacketed reaction tube, the aqueous phase is separated. The non-reacted divarinester is extracted by six-time addition of 1,000 g 1% aqueous sodium hydroxide. After acidification of the combined sodium hydroxide extracts with half concentrated sulphuric acid and re-extraction of this aqueous phase, approx. 30% (130 g) non-reacted divarinester are regained. Approx. 320 g cannabidivarincarbonsauremethylester (III) are in the toluene phase, which complies with a yield of approx. 50% in theory. This first intermediate product serves as starting compound for the subsequent transesterification.

Alternative: Coupling step with metal triflates
The above described coupling reaction is performed with zinc-trifluormethansulfonate instead of borontrifluorid*etherate.

Step 2: Transesterification/Synthesis of 2-hydroxyethyl-cannabidivarinolat (IV) (Preferred Compound of the Formula (A) as Described Herein):

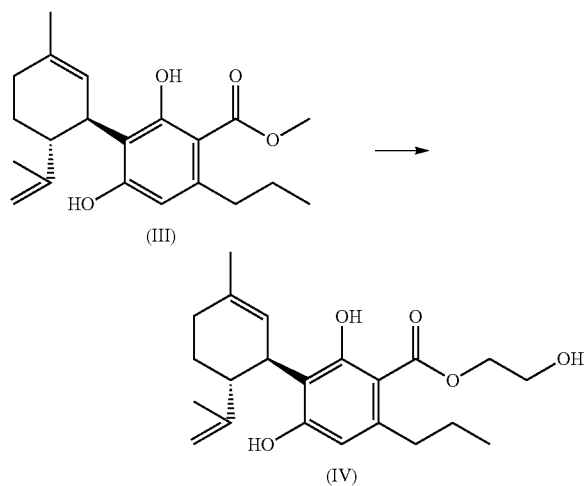

The toluene of the solution obtained in step 1 is removed by distillation and 650 g ethylenglycol are added to the remaining first intermediate product while stirring and the mixture is reacted with a solution of 122 g potassium hydroxide in 420 g ethylenglycol. A vacuum of approx. 0.5 bar is applied and the mixture is heated to 100-120° C. for 2 h, wherein approx. 40 g methanol are distilled off. The resulting product mix mainly comprises 2-hydroxy-ethyl-cannabidivarinolat (IV).

Step 3: Saponification/Decarboxylation, Synthesis of CBDV (V):

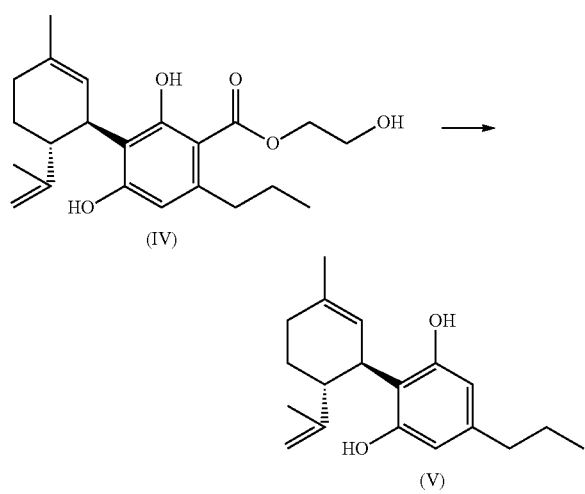

Afterwards the temperature is increased to 150° C. and it is stirred at this temperature for 3-4 h (also under vacuum; cf. step 2). The mixture is cooled down to approx. 40° C. and reacted with 1,500 g water as well as with 800 g methyl-tert.-butylether and for neutralisation approx. 180 g half concentrated sulphuric acid is added. After the phase separation, the solvent is evaporated using a rotary evaporator and the remains are distilled over a thin-film evaporator at a vacuum of approx. 1 mbar and a shell temperature of 230° C. 270 g cannabidivarin (CBDV) (V) are obtained in form of a viscous, yellowish oil with a purity of approx. 85%; which complies with a yield of 85% in theory related to the used cannabidivarincarboxylicacid ester. This viscous, yellowish oil is then recrystallized in 270 g n-heptane at approx. 10° C., whereupon 190 g white to slightly yellowish crystallisation with a purity of approx. 99% cannabidivarin (V) is obtained.

Step 4: Cyclization, Synthesis of THCV:

50 g pure cannabidivarin (V) are reacted with 40 g borontrifluorid*ether-complex in 250 g methylenchloride and at approximately 22° C. within 10 min while stirring. It is stirred for 20 min at said temperature and 200 g ice water are subsequently added, the organic phase is washed with sodium bicarbonate solution and the solvent is evaporated using a rotary evaporator. The remaining raw material of approx. 50 g contains approx. 74% THCV and approx. 26% side products. After column chromatographic purification, 30 g pure THCV are obtained, complying with a yield of approx. 60% in theory.

Synthesis of 2-Hydroxyethylcannabidivarinolat (IV) (Preferred Compound of the Formula (A) as Described Herein) Over the Divarinacidglycol Ester

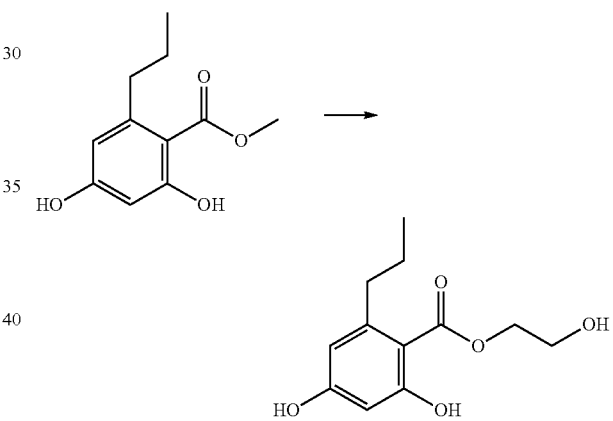

50 g (0.28 Mol) divarinacidmethyl ester are dissolved at RT in 100 g ethylenglycol, reacted with a solution of 17 g sodium hydroxide in 120 g ethylenglycol and heated to 80° C. for 2 h while stirring. The temperature is cooled down to RT, the reaction mixture is added on 200 g ice water, 200 g methyl-tert.butylether are added and the pH is set to 6 with half concentrated sulphuric acid while stirring. After the phase separation, the solvent is removed and a brownish coloured solid is obtained. This solid is recrystallized in the same amount of toluene, whereupon 42 g light crystallisation are obtained. Yield 60% in theory.

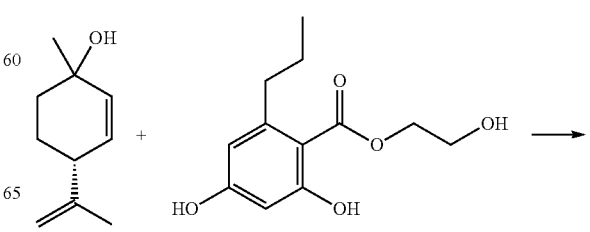

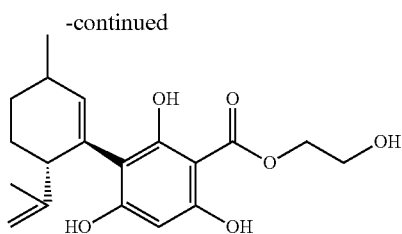

27 g (0.175 Mol) menthadienol and 42 g (0.175 Mol) divaringlycol ester are dissolved in 140 g acetonitrile at RT (250 mL solution A), likewise an adequate amount of borontrifluorid*etherate is solved in 63 g acetonitrile at RT (95 mL solution B). Via two separated dosing pumps, solution A with solution B is pumped with a constant stream into a stirred reaction cell in each case. From the reaction cell the reaction mixture flows via a PTFE-tube into a stirred 100 g sodium bicarbonate solution. The total reaction time is approx. 5 min. After the dosage, the hydrolysed reaction solution is stirred for approx. 30 min. After addition of 200 g, the settling aqueous phase is separated and the azeotropic mixture of toluene/acetonitrile is distilled off. For the separation of the non-reacted divaringlycol ester, the remaining are reacted with 200 g fresh toluene and extracted by four-time addition of 100 g 1% aqueous sodium hydroxide. After neutralisation of the toluene phase by washing with diluted aqueous sulphuric acid and removal of the toluene, 40 g raw product (IV) are obtained. With column chromatographic purification at silica gel (cyclohexane/ethyl acetate) pure 2-hydroxyethylcannabidivarinolat (IV) can be isolated.

This product can be converted to CBDV (V) after above described step 3.

Synthesis of n-hexylcannabidivarinolat over the divarinacid-n-hexyl ester

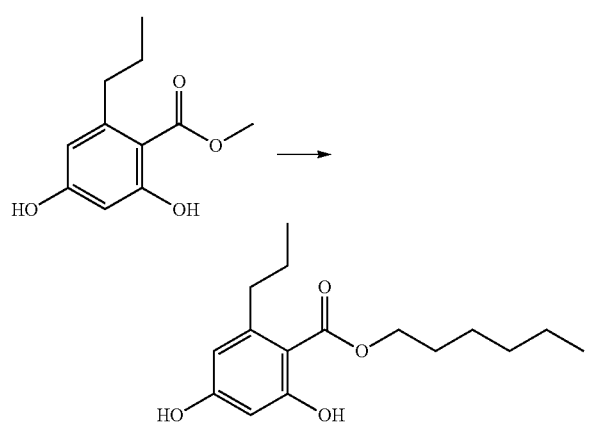

28 g (0.133 Mol) divarinacidmethyl ester are dissolved in 136 g n-hexanole at RT, reacted with 0.7 g (13 mMol) sodiummethylate and heated under reflux for 5 h while stirring. The hexanole is distilled off, 100 g toluene as well as, at RT, 100 g ice water are added and the pH is set to 6 with half concentrated sulphuric acid while stirring. After the phase separation the solvent is removed and it is recrystallized to cyclohexane, whereupon 28 g white crystallization are obtained. Yield 75% in theory.

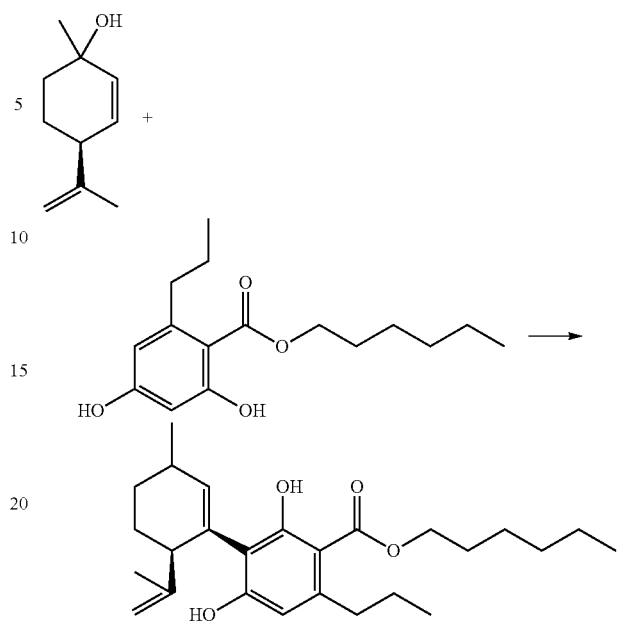

15 g (0.1 Mol) menthadienol and 28 g (0.1 Mol) divarinacid-n-hexyl ester are dissolved in 120 g toluene at RT (150 mL solution A), likewise an adequate amount of borontrifluorid*etherate is solved in 25 g toluene at RT (30 mL solution B). Via two separated dosing pumps, solution A with solution B is pumped with a constant stream of 7 mL/min into a stirred reaction cell in each case. From the reaction cell the reaction mixture flows via a PTFE-tube into a stirred 100 g sodium bicarbonate solution. Further purification is performed analogous to the above described example. Also here, the thus obtained raw product is purified column chromatographically at silica gel (cyclohexane/ethyl acetate).

This product can be converted to CBDV (V) after above described step 3.

Synthesis of Cyclohexylcannabidivarinolat Over the Divarinacid-Cyclohexyl Ester

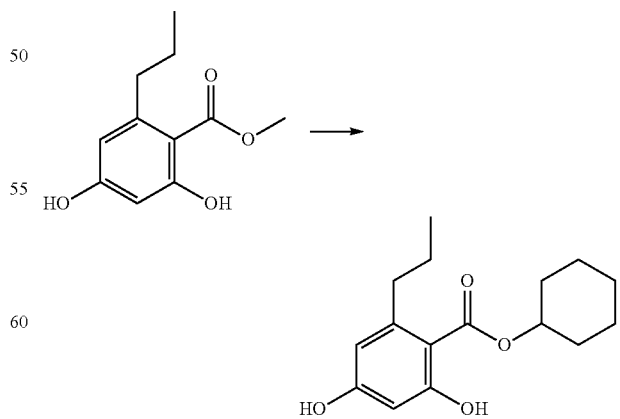

28 g (0.133 Mol) divarinacidmethyl ester are dissolved in 133 g cyclohexanole at RT and reacted analogously to above described. After the cristallisation of methyl-tert.-butyl ether, 26 g white cristallisation are obtained. Yield 70% in theory.

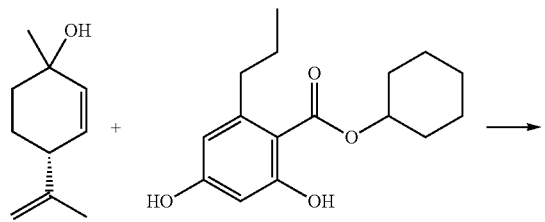

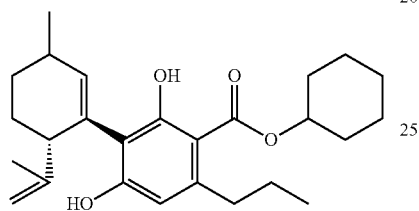

14 g (94 mMol) menthadienol and 26 g (94 mMol) divarinacid-cyclohexyl ester are dissolved in 120 g toluene at RT (150 mL solution A), likewise an adequate amount of borontrifluorid*etherate is solved in 25 g toluene at RT (30 mL solution B). Via two separated dosing pumps, solution A with solution B is pumped with a constant stream of 7 mL/min into a stirred reaction cell in each case. Further proceedings comply with the above described procedure. The thus obtained raw product is also purified column chromatographically at silica gel (cyclohexane/ethyl acetate).

This product can also be converted to CBDV (V) after above described step 3.

APPLICATION EXAMPLES

By means of the subsequent examples of preferred pharmaceutical formulations according to the invention, the application according to the invention of compounds of the formula (A) is further described. In this respect, the use of compound (IV) is preferred.

Application Example 1

Capsules according to the "*Neuen Rezeptur Formularium*", 18. supplement, 2001.

Mixture for 1 capsule

|  | 50 mg | 100 mg | 250 mg |
| --- | --- | --- | --- |
| Compound of the formula (A) | 0.05 g | 0.1 g | 0.25 g |
| Hard fat (adeps solidus) (slip melting point: 37-40° C.; OH-Number: 7-17; VS-Number: 245-260) | to 0.430 g | to 0.430 g | to 0.430 g |
| Hard gelatine capsule shell, Size 1 | 1 piece | 1 piece | 1 piece |

Mixture for 30 capsules including 10% surplus of the melt

|  | 50 mg | 100 mg | 250 mg |
| --- | --- | --- | --- |
| Compound of the formula (A) | 1.65 g | 3.3 g | 8.25 g |
| Hard fat (adeps solidus) (slip melting point: 37-40° C.; OH-Number: 7-17; VS-Number: 245-260) | to 14.2 g | to 14.2 g | to 14.2 g |
| Hard gelatine capsule shell, Size 1 | 30 pieces | 30 pieces | 30 pieces |

Mixture for 60 capsules including 5% surplus of the melt

|  | 50 mg | 100 mg | 250 mg |
| --- | --- | --- | --- |
| Compound of the formula (A) | 3.15 g | 6.3 g | 16.5 g |
| Hard fat (adeps solidus) (slip melting point: 37-40° C.; OH-Number: 7-17; VS-Number: 245-260) | to 27.1 g | to 27.1 g | to 27.1 g |
| Hard gelatine capsule shell, Size 1 | 60 pieces | 60 pieces | 60 pieces |

1. In a horizontally adjusted capsule filling machine the used hard gelatine capsule shells are opened, the fixed capsule bottoms are exposed and provided for being filled.

2. In a beaker a little more hard fat than necessary for the mixture is melted on the water bath. In-process examination: The hard fat melt must be clear at visual examination. It may be coloured slightly yellow.

3. In a second beaker molten hard fat is added to the compound of formula (A) til the indicated amount for the mixture. The substance is dissolved with a glass rod while stirring. In-process examination: The fat melt must be clear at visual examination. It may be coloured slightly yellow.

4. The fat melt is left on the warm but no longer boiling water bath until the last capsule is filled, or is removed from the water bath and warmed again as required. In-process examination (to be repeated occasionally): The temperature of the melt must be between 35 and 45° C.

5. Approximately 1 ml fat melt is brought up into a 1-ml-disposable syringe via a cannula with a preferably broad lumen (see section "pharmaceutical explanations—production technique and filling"). Immediately two capsule bottoms are filled.

In-process examination: The upper border of the capsule bottom must be completely wetted inside by the fat melt. The surface of the liquid must be flat or slightly arched to the inside (concave).

6. The syringe is refilled again and the filling of further capsules is continued as long as all capsule bottoms are filled. The empty space arising inside the capsules during the cool down of the melt may not be filled up. In-process examination: In the beaker only a small rest of approximately 1 ml fat melt may remain.

7. After solidification of the fat melt in the capsule bottoms, the capsules are tightly closed.

In-process examination: The surface of the fat melt must appear similarly opaque in all capsule bottoms.

End product examination: The closed capsules must look uniform. Only if required: The single masses of all capsules must be between 460 and 540 mg.

Application Example 2

Oily drops according to the "*Neuen Rezeptur Formularium*", 19. supplement, 2002.

| Ingredients | 20 g | 100 mass parts |
|---|---|---|
| Compound of the formula (A) | 5 g | 25 pieces |
| Medium-chain triglycerides | to 20.0 g | to 100.0 pieces |

1. The compound of the formula (A) is dissolved in the storage container with a suitable solvent.

2. The compound of the formula (A) is weighed in a beaker and dissolved in the medium-chain triglycerides while warming and stirring.

End product examination: The solution must be clear at visual examination. It may be coloured slightly yellow

The invention claimed is:

1. A mixture comprising one or more compounds of formula (A) and/or salts thereof

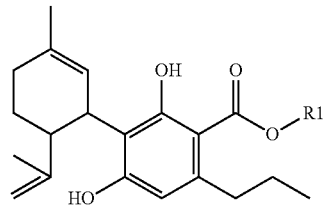

(A)

wherein $R^1$ is a $C_1$-$C_{15}$ aliphatic substituent optionally substituted with one or more hydroxyl groups, wherein the aliphatic substituent is
saturated or unsaturated,
branched or linear, and
acyclic or cyclic,
provided that if $R^1$ is an aliphatic substituent with no hydroxyl groups, the one or more compounds of formula (A) is/are selected from cyclohexylcannabidivarinolat, hexylcannabidivarinolat, salts thereof, and a mixture thereof.

2. The mixture according to claim 1, wherein the aliphatic substituent is saturated and/or linear.

3. The mixture according to claim 1 comprising a compound of formula (A-I)

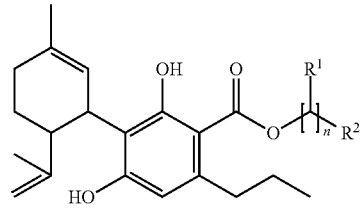

(A-I)

wherein,
each $R^1$ is independently H, a $C_1$-$C_2$ alkyl, or OH,
$R^2$ is H or OH,
n is an integer from 2 to 10,
provided that at least one of $R^1$ or $R^2$ is OH.

4. The mixture according to claim 1 comprising a compound of formula (A-II)

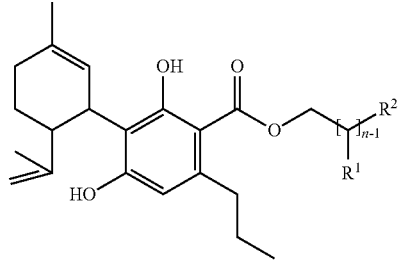

(A-II)

wherein,
each $R^1$ is independently H, a $C_1$-$C_2$ alkyl, or OH,
$R^2$ is H or OH,
n is an integer from 2 to 10,
provided that at least one of $R^1$ or $R^2$ is OH.

5. A mixture according to claim 1 comprising a compound of formula (A-III)

(A-III)

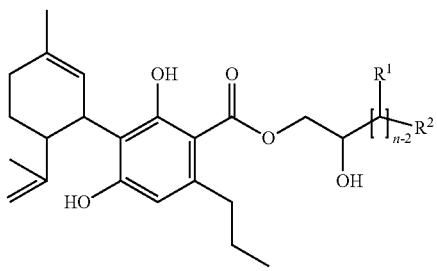

wherein, each $R^1$ is independently H, a $C_1$-$C_2$ alkyl, or OH, $R^2$ is H or OH, n is an integer from 2 to 10, provided that least one of $R^1$ or $R^2$ is OH.

6. The mixture according to claim 1 comprising a compound of formula (A-IV)

(A-IV)

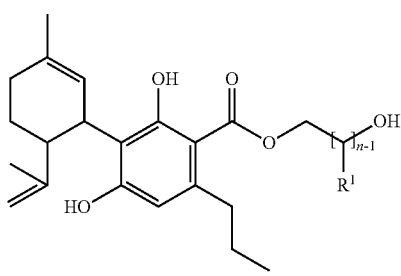

wherein each $R^1$ is independently H, a $C_1$-$C_2$ alkyl, or OH, and n is an integer from 2 to 10.

7. A mixture according to claim 3, wherein each $R^1$ of the compound of formula (A-I) is independently H or OH.

8. A mixture according to claim 4, wherein each $R^1$ of the compound of formula (A-II) is independently H or OH.

9. A mixture according to claim 5, wherein each $R^1$ of the compound of formula (A-III) is independently H or OH.

10. A mixture according to claim 6, wherein each $R^1$ of the compound of formula (A-IV) is independently H or OH.

11. A mixture according to claim 1, wherein the compound of the formula (A) is a compound of formula (IV):

(IV)

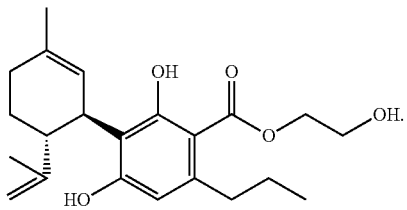 [SMILES: C=C(C)[C@@H]1CCC(C)=C[C@H]1c1c(O)cc(CCC)c(C(=O)OCCO)c1O]

12. A method for producing a mixture according to claim 1 comprising:

reacting an ester of the formula (IX)

(IX)

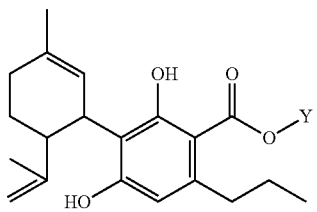

wherein Y is an organic substituent, with an alcohol of the formula HO—X, wherein X is a $C_1$-$C_{15}$ aliphatic substituent optionally substituted with one or more hydroxyl groups, wherein the aliphatic substituent is saturated or unsaturated, branched or linear, and acyclic or cyclic, provided that if X is an aliphatic substituent with no hydroxyl groups, the alcohol of formula HO-X is selected from cyclohexanol and hexanol;

wherein Y is different from X and selected such that the alcohol of formula HO—Y formed during the reaction boils at 1013 hPa at a lower temperature than the alcohol of formula HO—X.

13. A pharmaceutical or cosmetic formulation comprising a mixture according to claim 1.

14. A formulation suitable for consumption comprising a mixture according to claim 1.

15. The mixture according to claim 1 comprising a compound of formula (V) (cannabidivarin, CBDV):

(V)

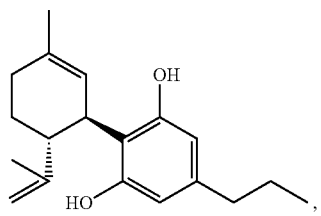

and/or a compound of formula (III) ((−)-trans-methylcannabidivarinolat):

(III)

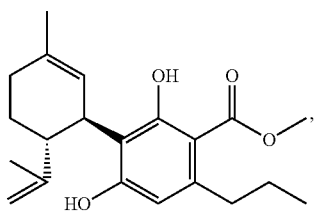

wherein if the mixture comprises a compound of formula (V), a molar ratio of a total amount of the one or more compounds of formula (A) and/or salts thereof to a total amount of the compound of formula (V) is greater than 1:1, and if the mixture comprises a compound of formula (III), a molar ratio of a total amount of the one or more compounds of formula (A) and/or salts thereof to a total amount of the compound of formula (III) is greater than 1:1.

* * * * *